US007626187B2

(12) United States Patent
Younts

(10) Patent No.: US 7,626,187 B2
(45) Date of Patent: Dec. 1, 2009

(54) METHOD AND APPARATUS FOR ERADICATING UNDESIRABLE ELEMENTS THAT CAUSE DISEASE, AILMENTS OR DISCOMFORT

(75) Inventor: George Younts, 6608 Ladyslipper La., Clifton, VA (US) 20124

(73) Assignee: George Younts, Clifton, VA (US)

( * ) Notice: Subject to any disclaimer, the term of this patent is extended or adjusted under 35 U.S.C. 154(b) by 375 days.

(21) Appl. No.: 11/439,221

(22) Filed: May 24, 2006

(65) Prior Publication Data

US 2006/0275171 A1 Dec. 7, 2006

Related U.S. Application Data

(60) Provisional application No. 60/686,442, filed on Jun. 2, 2005.

(51) Int. Cl.
*A61L 2/10* (2006.01)

(52) U.S. Cl. ............................ 250/504 H; 250/455.11; 422/24

(58) Field of Classification Search ...................... None
See application file for complete search history.

(56) References Cited

U.S. PATENT DOCUMENTS

| | | | |
|---|---|---|---|
| 4,366,125 | A | 12/1982 | Kodera |
| 4,396,582 | A | 8/1983 | Kodera |
| 4,424,188 | A | 1/1984 | DiGeronimo |
| 4,448,750 | A | 5/1984 | Fuesting |
| 4,591,485 | A | 5/1986 | Olsen et al. |
| 4,728,368 | A | 3/1988 | Pedziwiatr |
| 5,120,499 | A | 6/1992 | Baron |
| 5,547,635 | A | 8/1996 | Duthie, Jr. |
| 5,626,822 | A | 5/1997 | Kadowaki et al. |
| 5,807,521 | A | 9/1998 | Franetzki |
| 6,071,473 | A | 6/2000 | Darwin |

(Continued)

FOREIGN PATENT DOCUMENTS

| | | |
|---|---|---|
| CN | 1440817 | 9/2003 |

(Continued)

OTHER PUBLICATIONS

Development and design of process modules for ballast water treatment onboard; Kornmeuller; Abstracts of $2_{nd}$ International Ballast water treatment R&D Symposium, London, Jul. 2003; p. 42.

(Continued)

*Primary Examiner*—Elizabeth L McKane
(74) *Attorney, Agent, or Firm*—Nixon & Vanderhye

(57) ABSTRACT

A system for eradicating or neutralizing undesirable elements such as organisms or insects on or in a particular article to prevent harm to humans or animals coming in contact with or exposed to the article, comprising exposing predetermined surfaces of the article to a predetermined ultraviolet radiation to kill or neutralize undesirable elements on the surfaces of the article; and thereafter applying to the surfaces of the article an eradication technology treatment to further kill, neutralize and/or drive out and expose undesirable elements. After the application of the eradication technology treatment, the article surfaces may be exposed to a second ultraviolet radiation to kill or neutralize any remaining exposed undesirable elements. The apparatus may be in the form of a hand-held device, mobile modular units, or a large unit on a trailer or in a fixed location.

11 Claims, 10 Drawing Sheets

U.S. PATENT DOCUMENTS

| | | | |
|---|---|---|---|
| 6,074,565 | A | 6/2000 | Buckner |
| 6,090,346 | A | 7/2000 | Rose et al. |
| 6,228,332 | B1 | 5/2001 | Dunn et al. |
| 6,391,117 | B2 | 5/2002 | Suzuki |
| 6,555,011 | B1 | 4/2003 | Tribelsky et al. |
| 6,576,188 | B1 | 6/2003 | Rose et al. |
| 6,736,979 | B2 | 5/2004 | De Meulenaer et al. |
| 6,790,409 | B1 | 9/2004 | Nakamura et al. |
| 6,845,971 | B2 | 1/2005 | Bachert |
| 7,160,566 | B2 * | 1/2007 | Fink et al. .................... 426/235 |
| 2002/0085947 | A1 | 7/2002 | Deal |
| 2002/0159917 | A1 | 10/2002 | Swart et al. |
| 2002/0197184 | A1 | 12/2002 | Palaniappan |
| 2003/0127753 | A1 | 7/2003 | Bachert |
| 2003/0133852 | A1 | 7/2003 | Hung |
| 2003/0192485 | A1 | 10/2003 | Opfel |
| 2004/0022668 | A1 | 2/2004 | Kitchen |
| 2004/0118427 | A1 | 6/2004 | Palfy et al. |
| 2004/0120845 | A1 | 6/2004 | Potember et al. |
| 2004/0202570 | A1 | 10/2004 | Nadkami |
| 2005/0072449 | A1 | 4/2005 | Alpert et al. |

FOREIGN PATENT DOCUMENTS

| | | |
|---|---|---|
| CN | 1482405 | 3/2004 |
| DE | 10006672 | 8/2001 |
| DE | 10200812 | 11/2003 |
| JP | 6296944 | 10/1994 |
| JP | 407047088 A | 2/1995 |
| JP | 7143999 | 6/1995 |
| JP | 2004016919 | 1/2004 |
| JP | 2004066208 | 3/2004 |
| WO | WO 03004421 | 1/2003 |

OTHER PUBLICATIONS

Wastewater disinfection using ultrasound and UV light; T. Blume et al. TU Hamburg-Harburg Reports on Sanitary Engineering 35, 2002; Neis U. (ed): Ultrasound in Environmental Engineering II.

Air Decontamination; G. Lesavoy and Jordan Peccia, Ph.D., PE; prior art.

Standardization of Methods for Fluence (UV dose) Determination in Bench-Scale UV Experiments; James R. Bolton & Karl G. Linden, M.ASCE[2]; Journal of Environmental Engeering © ASCE/Mar. 2003.

* cited by examiner

METHOD AND APPARATUS FOR ERADICATING UNDESIRABLE ELEMENTS THAT CAUSE DISEASE, AILMENTS OR DISCOMFORT

CROSS-REFERENCES TO RELATED APPLICATIONS

This application claims the priority of Provisional Patent Application No. 60/686,442 filed on Jun. 2, 2005.

STATEMENT REGARDING FEDERALLY SPONSORED RESEARCH OR DEVELOPMENT

N/A

BACKGROUND OF THE INVENTION

1. Field of the Invention

The present invention relates to a system (method and apparatus) for eradicating undesirable elements, such as organisms or insects, that cause disease, ailments, discomfort or the like and, more particularly, to such a system that utilizes multiple technologies in portable or fixed units for such eradication.

2. Description of the Background Art

In this country and worldwide there exists a major requirement to sterilize, eradicate and/or cause neutralization (destroy or disturb DNA structure) of mold spores, yeasts, bacteria, germs viruses, and relatively larger aggressive organisms e.g., dust mites, bugs and other hostile organisms all of which are the sources and/or cause of many human ailments from a level of annoyance, aggravation, illness, sickness to causing fatalities at limited to catastrophic levels. Current methods of control and eradication are limited mostly to aerosol or powder germicides or germicidal lamps, e.g., ultraviolet C band lamps (UVC). They are also disruptive and time consuming, and therefore extremely costly in direct and secondary cost. In certain situations these existing techniques are only partially effective or cannot be readily applied because of hazards and/or restricted or limited access to the source of the organisms. Some surfaces allow the organisms to be concealed or move to cover, e.g., fabrics, cracks, etc. The goal, of course, in most cases is to completely eliminate or neutralize the organisms, that is to achieve 100% effectiveness or as close to it as possible, or better than current techniques.

An object of the present invention is to neutralize, remove and/or kill mobile non-air borne mold, bacteria, bugs, insects, odors or the like that may have infested materials e.g., cloth, stuffing, filling, fabric, surfaces, joints, cracks or the like. It is necessary to remove all elements that cause illness, infection, allergic reactions and other problems that could be experienced by a person rubbing, touching, smelling or by other means of close contact. The popular air borne cleaners only act against some of these elements and of course they must be air borne. Most sterilizers are fixed or have limited mobility. Some of the known cleaners generate ozone which is suspected of having detrimental health effects in certain cases. The known heating and steaming techniques can have undesirable secondary effects and germicidal spray systems are restricted for health reasons. In many situations the undesirable targeted elements affix themselves, for nesting and dormant periods in their life cycle to solid materials, e.g., fabric, cracks, etc. Therefore, it is necessary that the treated surface be cleaned down to micron size, for example, nanometer (10-9↑ meters).

The system of the present invention is not subject to the disadvantages of the eradication systems known in the prior art and possesses many advantages not found in known systems.

SUMMARY OF THE INVENTION

In accordance with the present invention, the system is constructed to enable the selection of the most effective sub systems or technologies in singular or in combination form for the task in hand and to integrate them into an operable system tailored specifically for a particular eradication requirement. In this manner, the maximum benefit is achieved from available technologies and various combinations of technologies that are the most suitable for a particular task. The new and improved construction of the present system allows for new technologies to be readily incorporated therein as they become known or available.

The present system can be operated by using separate units independently or in combination to disturb, expose, destroy, disable and/or kill any undesirable elements, such as organisms or insects, that can cause illness or discomfort if a person is exposed to or comes in contact with them. Multiple technologies for eradication can be housed in separate units, such as plug-in units, to be available for individual use or in various combinations with other units in a desired sequence, depending on the eradication required.

These technologies are 1) controlled (continuous, pulsed,) ultraviolet lamp (UVC); 2) pulsed or steady state (continuous) ultrasound, 3) hypersonic (combination ultrasonic and auditable sonic) wave; 4) non-contact ultrasonic (NCU) and direct contact ultrasonic, (DSU); 5) application of ferrous micro-particles (<1 micron) by ultrasonic means into or impregnating elements to be destroyed; 6) quantum cascade, QC, laser; 7) infrared light LED; 8) UV-C LED; 9) laser diode and; 10) electro-magnetic field, EMF, force; or any combination of any of these. The separate or plug-in units to the extent possible have commonality of support connections, mounting modes, operational features (displays, power supplies, indicators, closed circuit television monitoring, etc.) and human-factor design.

The eradication technologies to be used are provided in separate units which can be singular or in combinations of two or more selected on the basis of operating conditions and targeted undesirable elements. The unit for one or more technologies may be constructed to plug into a universal eradicator mount or the like which will allow for the adding of new technology units or sub-units without requiring a significant modification of the system. The combination of the separate units or sub-units allows for quickly and easily selecting and integrating the appropriate sub system for specific eradication requirements. In this manner, the present system is effective in specialized ways of neutralizing and/or eradicating undesirable organisms and insects and can be easily adapted to different size applications.

The eradication system of the present invention can be provided in different embodiments. For example, the system may be provided in three different physical configurations. The first configuration is a hand-held wand unit with a portable or backpack support system which can be directed easily against small and narrow cracks, joints and crevice requirements. A second configuration is a portable or backpack support system to which is attached a series of interconnected modules or sub-units that can be moved by hand or a servo drive motor. For large applications, a third configuration utilizes a pod housing with scanners supporting eradicator sub-units of two or more eradication technologies. The pod housing could be mounted on a flat bed truck or the like for portability or could be placed in a fixed location at a facility using the eradication system. The pod may be provided with a movable bed for supporting a large object to be treated, e.g., a mattress, or the scanners may be movable.

DETAILED DESCRIPTION OF THE INVENTION

Figure 1:
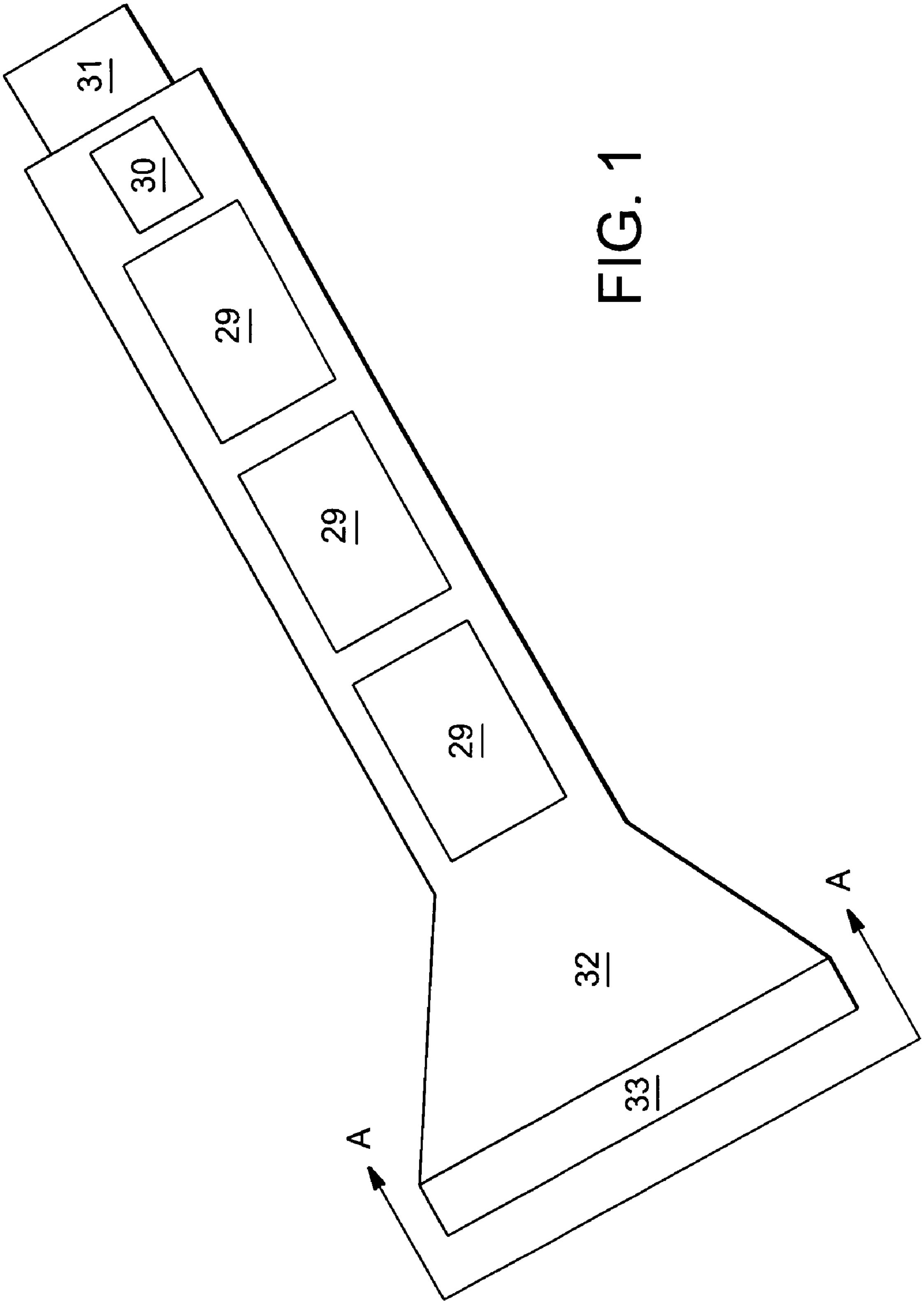
FIG. 1 is a schematic view of a first embodiment of the present invention in the form of a hand-held wand configuration.
Figure 2:
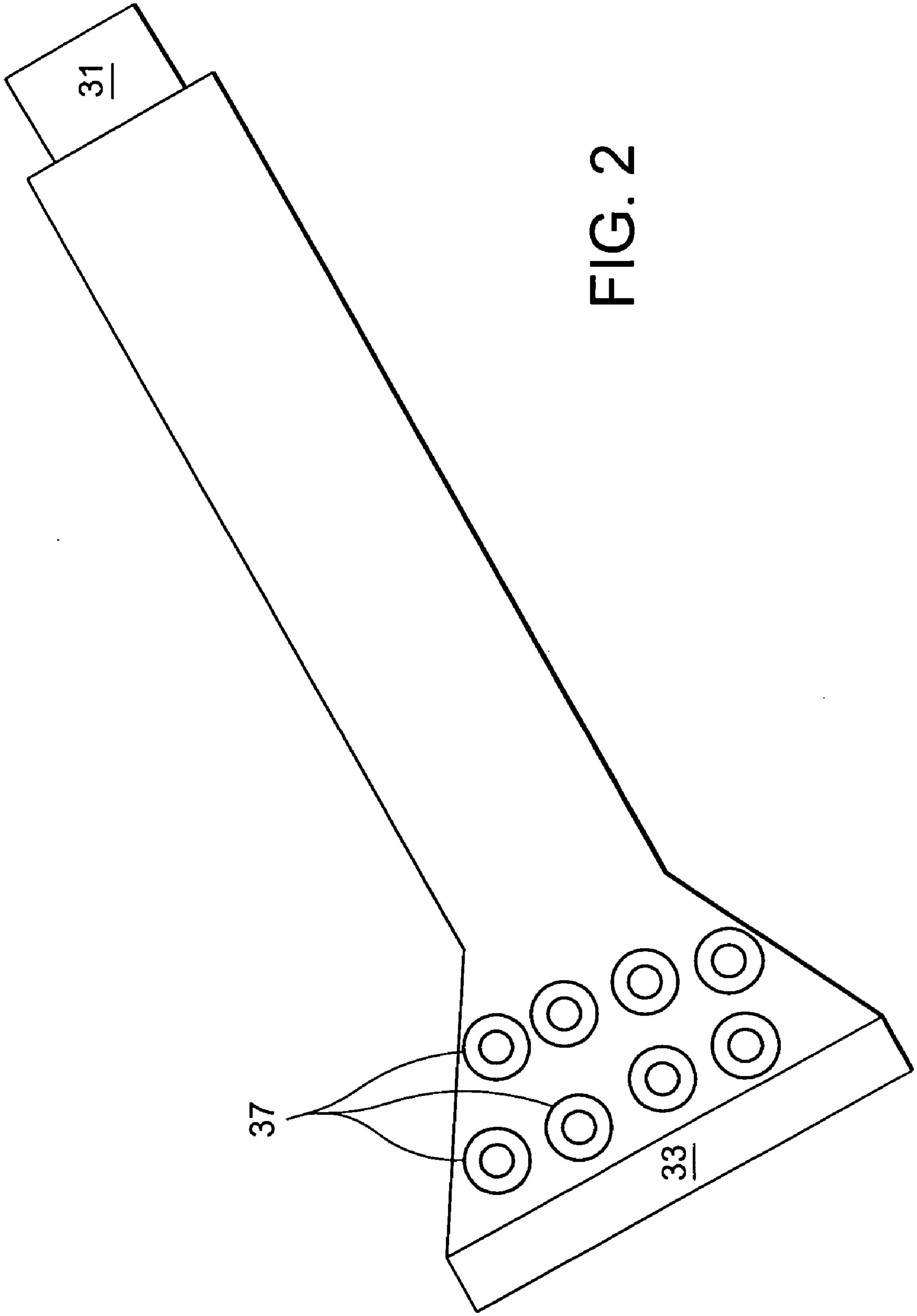
FIG. 2 is a schematic view of the first embodiment of FIG. 1 showing the external controls.
Figure 3:
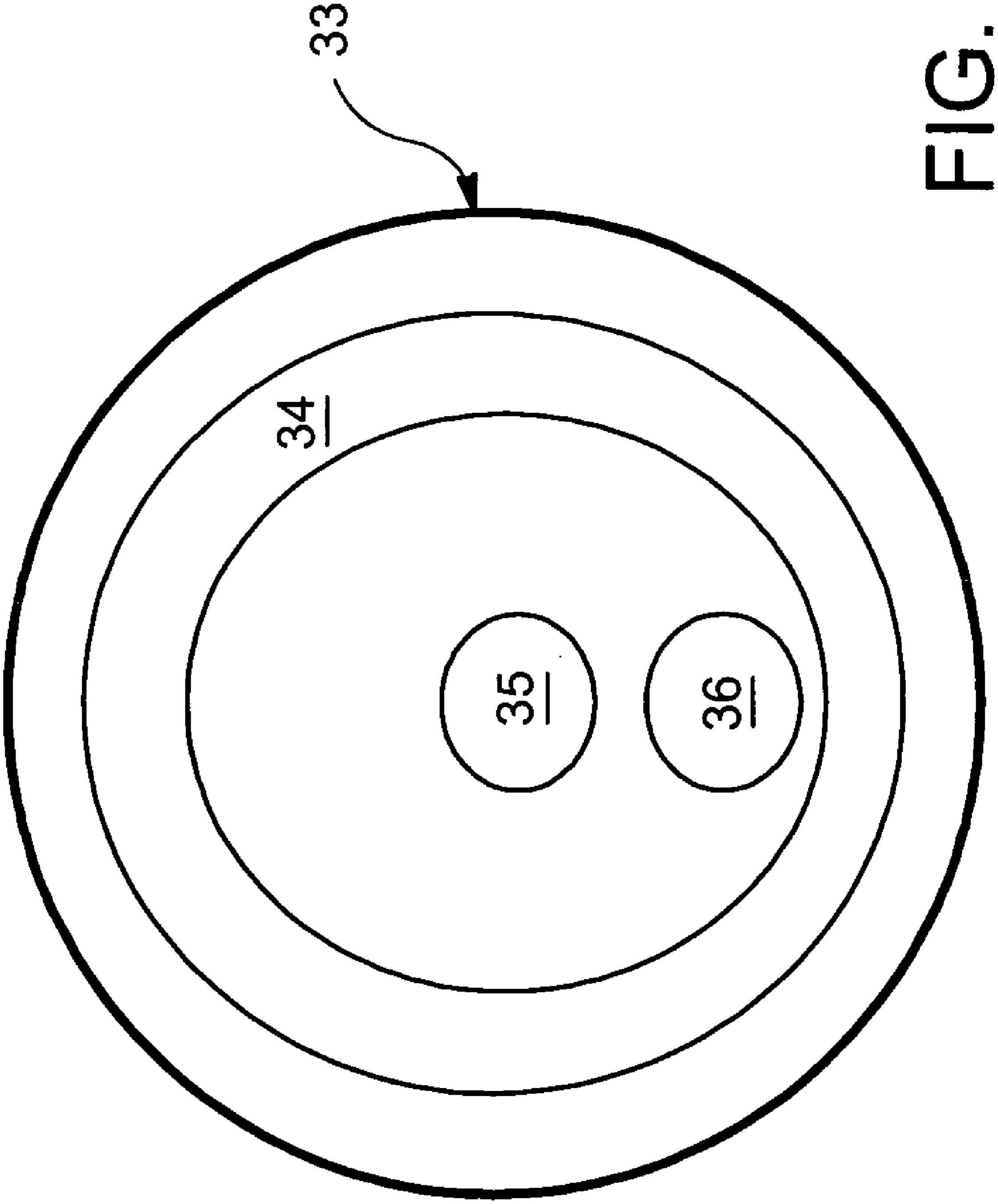
FIG. 3 is a schematic end view of the first embodiment shown in FIGS. 1 and 2, showing different eradication technologies embodied therein.
Figure 4:
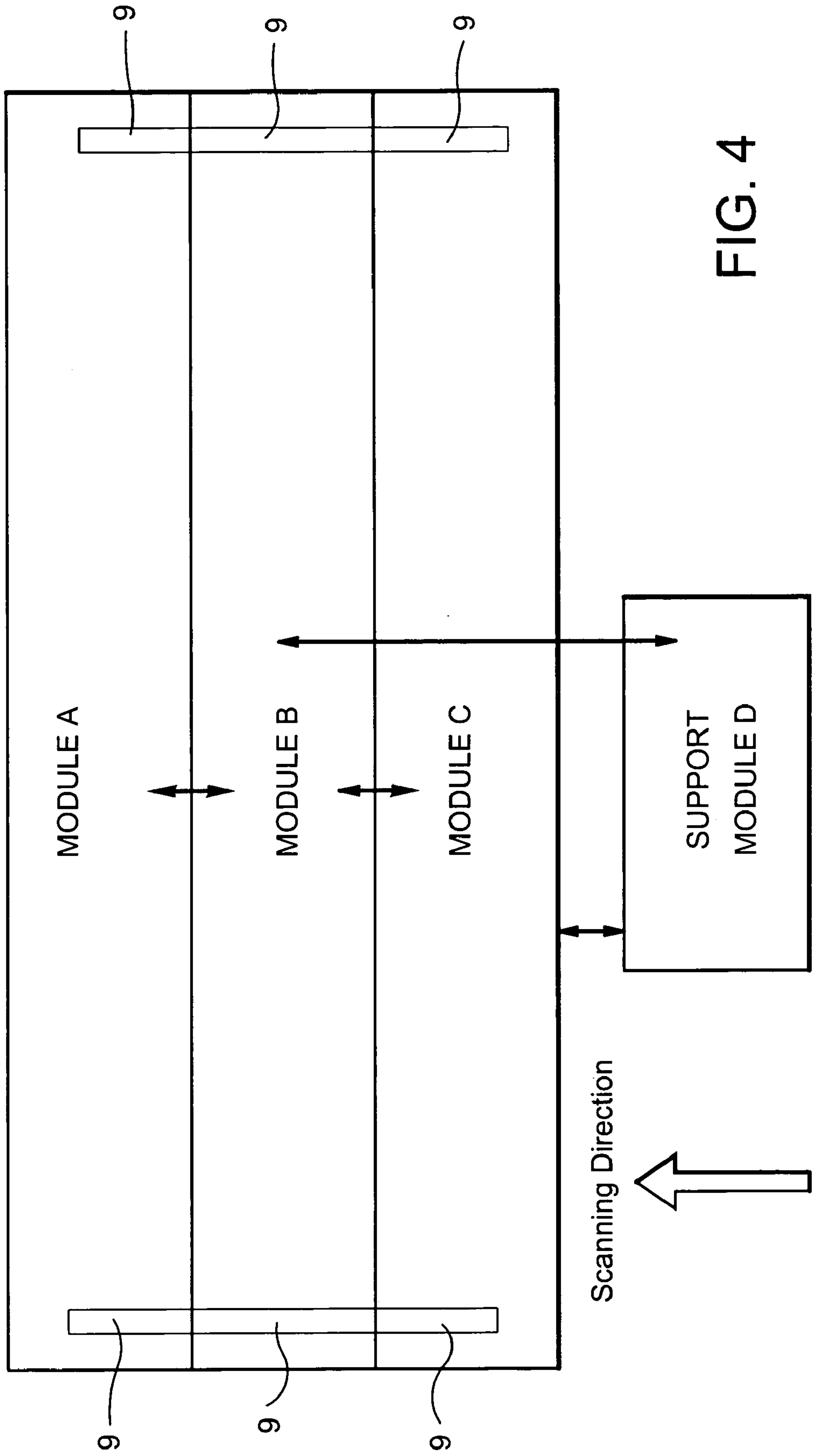
FIG. 4 is a schematic view of a second embodiment of the present invention wherein modular units are constructed to be connected to each other and to a support module.

FIGS. 1-3 illustrate a first embodiment of the present invention in the form of a hand-held wand configuration that can be used for interim treatment or quick eradication of small infested areas and treatment of small items such as sleeping bags, clothing, stuffed items or the like. The wand generally comprises a housing 32 having a sensor array 33 on the outer end thereof, miniaturized technology eradication units 29 of the same or different types removably mounted thereon, such as in a plug-in construction, a closed circuit TV interface 30 and an electronic and power support unit 31 that may be connected to a portable or backpack power source (not shown). As shown in FIG. 2, the wand may comprise a plurality of hand actuated controls 37 on the outer portion of the housing 32. Referring to FIG. 3, as an illustrative example, the sensor array 33 may comprise a UVC lamp 34, an ultrasound transducer 35 and a closed circuit TV camera 36.

FIGS. 4-8 illustrate a second embodiment of the present invention which comprises a modular compartmented component construction, with the number of separate units or components being varied depending on design factors and the particular eradication application. As an illustrative embodiment, this embodiment is described herein with respect to three modules and a support module as follows:

Module A: (Stage 1) Preliminary eradication/conditioning

Module B; (Stage 2) Selectively has installed one or a combination of the above-described eradication technologies, e.g., ultrasonic.

Module C: (Stage 3) Final eradication radiation with assessment, testing and viewing.

Module D: Support module and equipment.

Modules A, B, and C may be attached together in various combinations, e.g., plug-in units, and Support Module D may be a stand alone, movable support unit or may be provided in a backpack or the like. For example, Module A could house ultraviolet light miniature plug-in units (MPUs) in lamp or LED form and is attached to Module B; Module B could house any one or more of the ten MPUs described above, e.g., the ultrasonic sound wave source; and Module B is attached to Module C which may be similar to Module A. These modules may be supported by or connected to Support Module D in any suitable manner, e.g., by cables for microscopic metallic particles, air, electronics, and/or power. This three Module in-line assembly system embodiment may be placed on top of the material to be sanitized or cleaned, with Module A being pointed in the direction of movement. It is activated and moved slowly by hand over the surfaces to be treated or, in a fixed embodiment, movement could be servo motor driven in a preprogrammed pattern of scanning. In this manner, the material to be treated first is subjected to a controlled intense UV radiation from Module A. This kills or neutralizes some or all of the exposed undesirable elements. Then as Module B is moved laterally into place, the ultrasonic pressure wave drives out or kills directly those elements that were concealed from Module A radiation. Alternatively, an ultrasonic pressure wave of microscopic ferrous particles in Module B would impregnate the undesirable elements. The ultrasonic particulate wave sound penetrates the material and either kills or drives any of the undesirable elements into the open so that when Module C scans the material the controlled intense UV light completes the destruction of the undesirable elements. If the surface to be cleaned is particularly difficult, then another Module B with a different sub-unit eradicator of the type described herein, e.g., an ultrasonic pressure wave could be used. Instead of having an A, B, C system configuration, therefore, it could be an A, B, B system configuration or any other suitable configuration.

Module A

Figure 5A:
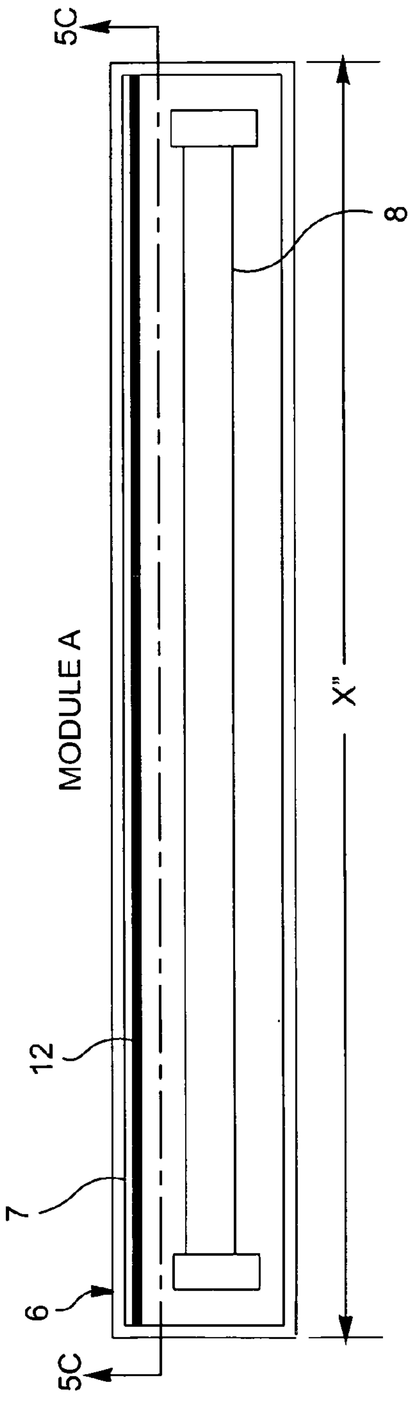
FIG. 5*a* is a bottom view of module A shown in FIG. 4.
Figure 5B:
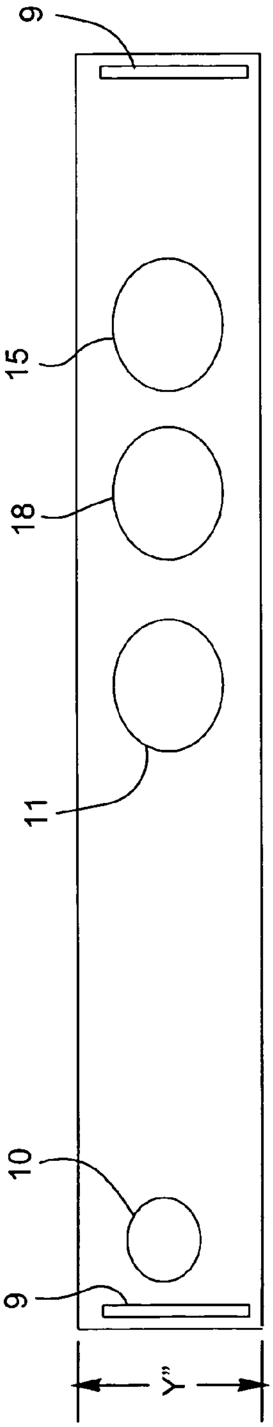
FIG. 5*b* is a top view of module A.
Figure 5C:
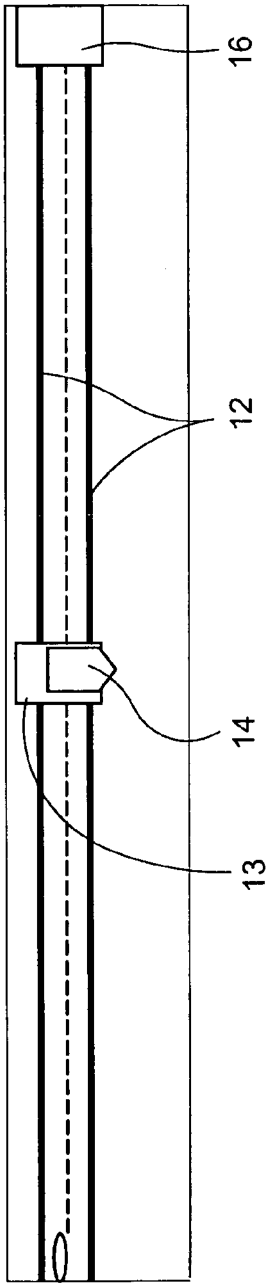
FIG. 5*c* is a sectional view taken substantially along line A-A in FIG. 5*a;*

Module A serves as the pre-conditioning sub-system destroying the open and apparent hostile organisms. Referring to FIGS. 5*a*, 5*b* and 5*c*, Module A comprises a housing or container 6 that is impervious to deterioration effects due to ultraviolet (UV) radiation. It is coated on the inside with a reflective coating 7 of any suitable type to enhance the reflection of any of the high intensity germicidal lamp 8 which may be approximately 18 inches long. An LED UVC source could be substituted for the lamp 8. Effectiveness of the eradication is a factor of both speed (period of exposure), light intensity, and wavelength. Different results could be expected from pulsed and steady state radiation. Generally, a dosage of 16,000 microwatts seconds per square centimeter or greater is required. To control the period of exposure and for general handling, Module A may be equipped with handles 9, e.g., stainless steel, on each end of the module for manual movement. Alternatively, Module A may be equipped with variable speed traction drives with a pacing indicator. This allows for control of the periods of exposure in an easier and more uniform manner. The other factor, light intensity, is controlled by use of different wattage lamps and a combination ON-OFF dimmer switch 10. Light wavelength (λ) of the UVC lamp, e.g., is in the range from 100 nanometers (nm) to 280 nm. A light intensity meter 11 allows for setting the lamp at a desired intensity level and ensures that the level is maintained with aging or different lamps. A special filtered viewing window 18 allows the operator to check if the lamp is illuminated and view the CCD camera 14 movement to see if it is operating properly. A heat exhaust fan with filter may be provided on one end of the module with the other end of the module, being vented with a filter.

A linear slide track 12 is mounted along the full length of the back wall of Module A. A detachable mount 13 on the track 12 holds a very high (millimeters) resolution micro-miniaturized CCD video camera 14. A chain or cable linkage attached to a servo or motor 16 and wrapped around a pulley at other end allows for the movement of the CCD mount 13 from one end to the other on the slide track 12. A camera control 15 enables the operator to position the camera mount to any point, left or right, on the slide track and to tilt it up or down. The control 15 can be set to a continuous variable modem to move the mount 13 from one end to the other, automatically reversing at each end. The CCD video camera 14 can be attached to the mount 13 in any suitable manner for easy install or removal for exchange or maintenance. A toggle switch can be provided to allow the user to pan (scan) the camera from right to left to right and set the switch to fix or continuous panning.

Module B

Figure 6A:
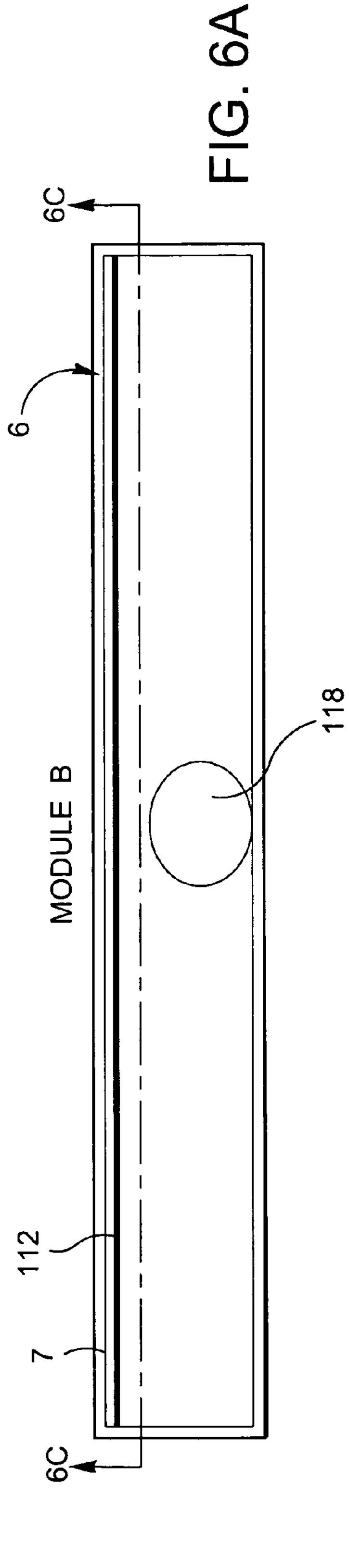
FIG. 6*a* is a bottom view of module B shown in FIG. 4.
Figure 6B:
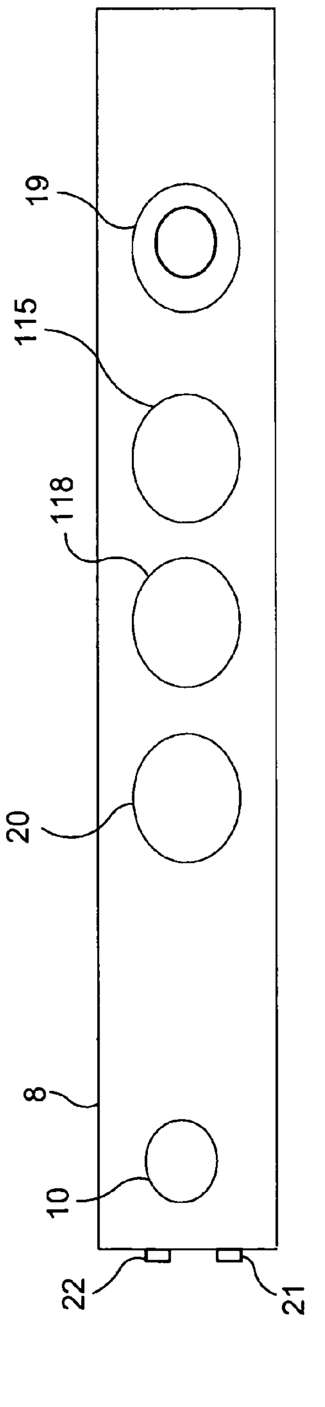
FIG. 6*b* is a top view of module B.
Figure 6C:
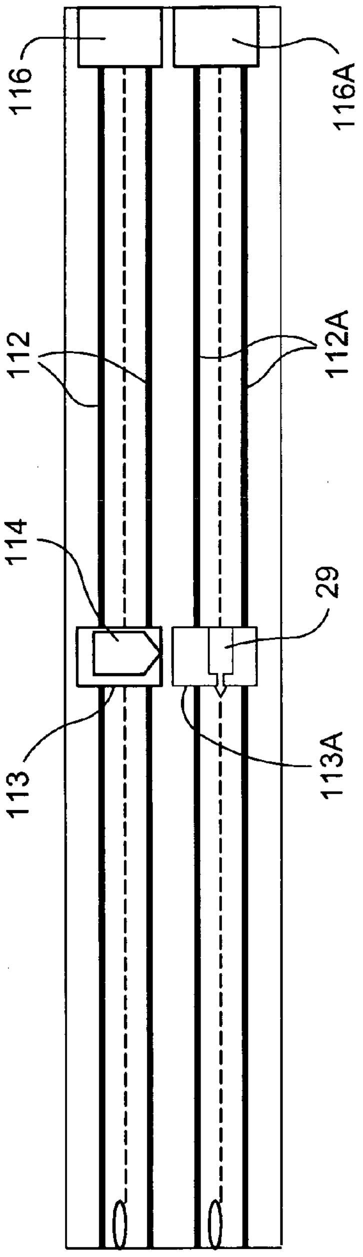
FIG. 6*c* is a sectional view taken substantially along line B-B in FIG. 6*a;*

Module B serves to destroy or neutralize any undesirable elements remaining after the Module A treatment. The Module B housing may be the same as or similar to the Module A housing, and is illustrated in FIGS. 6*a*, 6*b* and 6*c*. In one embodiment, it has two slide tracks 112, 112*a* mounted on the back wall thereof. One track is for the video camera and the second track is for mounting of the destructor subunit. Each slide track is attached along the full length of the module's back wall. The track 112 supports a detachable mount 113 to hold a very high (millimeters) resolution micro-miniaturized CCD video camera 114). A chain or cable linkage is attached to a servo or motor 116 and wrapped around a pulley at other end to allow for moving the CCD mount 113 from one end to the other on the slide track 112. A camera control 115 enables the operator to position the camera mount to any point, left or right, on the slide track 112 and to tilt it up or down. The control 115 can be set to a continuous variable drive mode to move the mount 113 from one end to the other, automatically reversing at each end. The CCD video camera 114 can be attached to the mount 113 in any suitable manner for easy install or removal for exchange or maintenance. A toggle switch may be provided to allow the user to pan (scan) the camera from right to left to right and set the switch to fix or continuous scanning.

A second similar assembly comprising the linear slide track 112*a* with detachable mount 113*a* and drive chain/cable linkage with servo or motor 116*a* is mounted just below the CCD camera drive track assembly 113, 112, 116. A second set of controls may be provided to perform the same functions as those for the CCD video operation as described above. Positioning right or left on track, scanning left and right, tilting up or down and being set to manual or automatic operation. The mount 113*a* is used in this case to support one of the plug-in eradicator units 29 described above. MPUs would be one or more of the ten technologies described above.

A servo or motor control can be provided to move the camera mount, hence the camera, so that it can be automatically moved back and forth the full length of the slide track. The speed can be controlled to allow the dwell time of the camera to be variable. The same control can also be set to manual and thereby it will be possible to place the camera mount at a fixed location anywhere on the slide track. The camera can be tilted up or down by manual control. A special filtered viewing window 118 allows the operator to check if the lamp is illuminated and view the CCD camera to see if it is operating properly. For example, if an ultrasonic ferrous micro particle spray subunit is placed on the mount of the second drive and directed toward the material being treated, it will destroy any residual hostile organisms that were concealed from Module A UVC and/or those more tightly bonded will be disturbed enough to become exposed. The micro particles will also penetrate any mold or more solid organisms which can be less susceptible to UVC.

In one example, the Module B may comprise an ultrasonic nozzle-less spray subunit (TM-, USI. UltrasonicSystems, Inc. www.ultraspray.com) or a variation of the technology. This nozzle-less spray subunit is capable of taking loose ferrous particles and creating a fan shaped pattern of extremely small size which would strike the surface with the pressure of the ultrasonic frequency wave motion and impregnate the targeted elements. Applying an agitating electromagnetic field would disturb the elements and kill them because of the impregnated elements or force them into the opening where a UV or other radiating beam device would kill them. The nozzle-less spray unit is constructed to easily attach to the mount 113*a* which in turn is attached in an easily removable way (for exchange or maintenance) to the linear slide track 113*a*. The mount 113*a* is attached to a motor or servo drive linkage 116*a* to allow for movement of the nozzle mount, hence the nozzle-less spray, automatically back and forth the full length of the slide track. The speed can be varied to allow the dwell time of the nozzle to be set for the particular particles being discharged. The same control can also be set to manual and thereby it will be possible to place the nozzle mount at a fixed location anywhere on the slide track. The spray pattern also may be adjustable to set the fan shape as circumstances dictate. The nozzle requires connection to a source of air 22 and ferrous particle supply 21, which would be provided from the mobile Support Module D assembly. A particulates control 20 may be provided.

A control 19 on Module B allows for turning the air supply and particle supply ON or OFF. There is also a control 27 to tilt the nozzle up and down for optimum coverage. The ultrasonic signal amplifier part of the control electronics package 23 may be located in the Support Module. The exact ultrasonic frequency to be used would be determined from testing. Maximum coupling is a factor of wavelength λ (wavelength)= speed of sound (1100 feet per second) divided by frequency (in hertz)] and if dust mites, for example, are on the average 4 mm long, then an ultrasonic signal at approximately 80 KHz would be necessary. Some experimentation would be necessary to determine exactly what frequencies are most effective against the hostile organisms of interest. A multi-frequency ultrasonic signal switch in Module D able to be set to several fixed frequencies or set on an automatic multi-frequency scanning mode at a variable scan rate may be provided. The particle supply can be any one of several commercially available mixtures for cleaning, deodorizing, odorizing, or a combination of one or more of these. The system is constructed to use various size particles. For example, a change of the ultrasonic plug-in spray unit could provide for the use of medium to high density particles. The system also enables the attachment of different types of dispersal units for spraying other types of germicidal products.

Module C

Figures 7A, 7B, 7C:
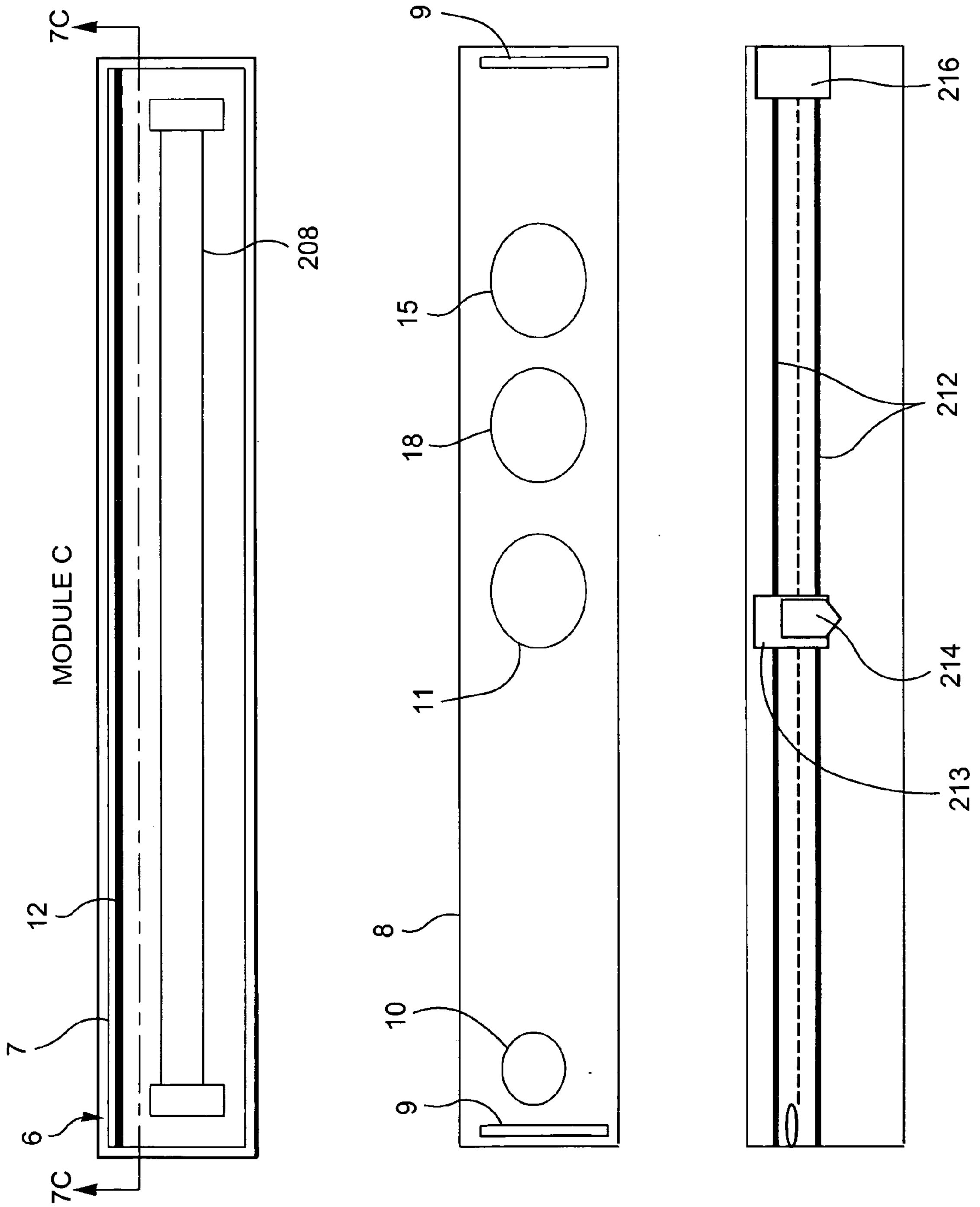
FIG. 7*a* is a bottom view of module C shown in FIG. 4.
FIG. 7*b* is a top view of module C.
FIG. 7*c* is a sectional view taken substantially along line C-C in FIG. 7*a;*

As shown in FIGS. 7*a*, 7*b* and 7*c*, Module C is very similar to Module A in construction. It is equipped with a germicidal UVC lamp or LED 208 and CCD video camera 214 and serves as a final scanning device and quality assurance checker. The high resolution microminiaturized CCD video camera 214 is installed on a mount 213 and slide track 212, and may be movable by a servo-motor 216 in the same manner as that herein described for Module A. The controls for the use of Module C are the same or similar types as those for Module A. A close inspection of the treated material with the camera 214 will reveal any remaining contaminants. A heat exhaust fan with filter may be mounted on one end of the module and the other end of the module may be vented with a filter. Module C may also be equipped with a vacuum to remove eradicated particles and deposit them in a small container mounted on the exterior thereof. When necessary, the container can be emptied into a larger container located in Support Module D.

Module D

Figure 8:
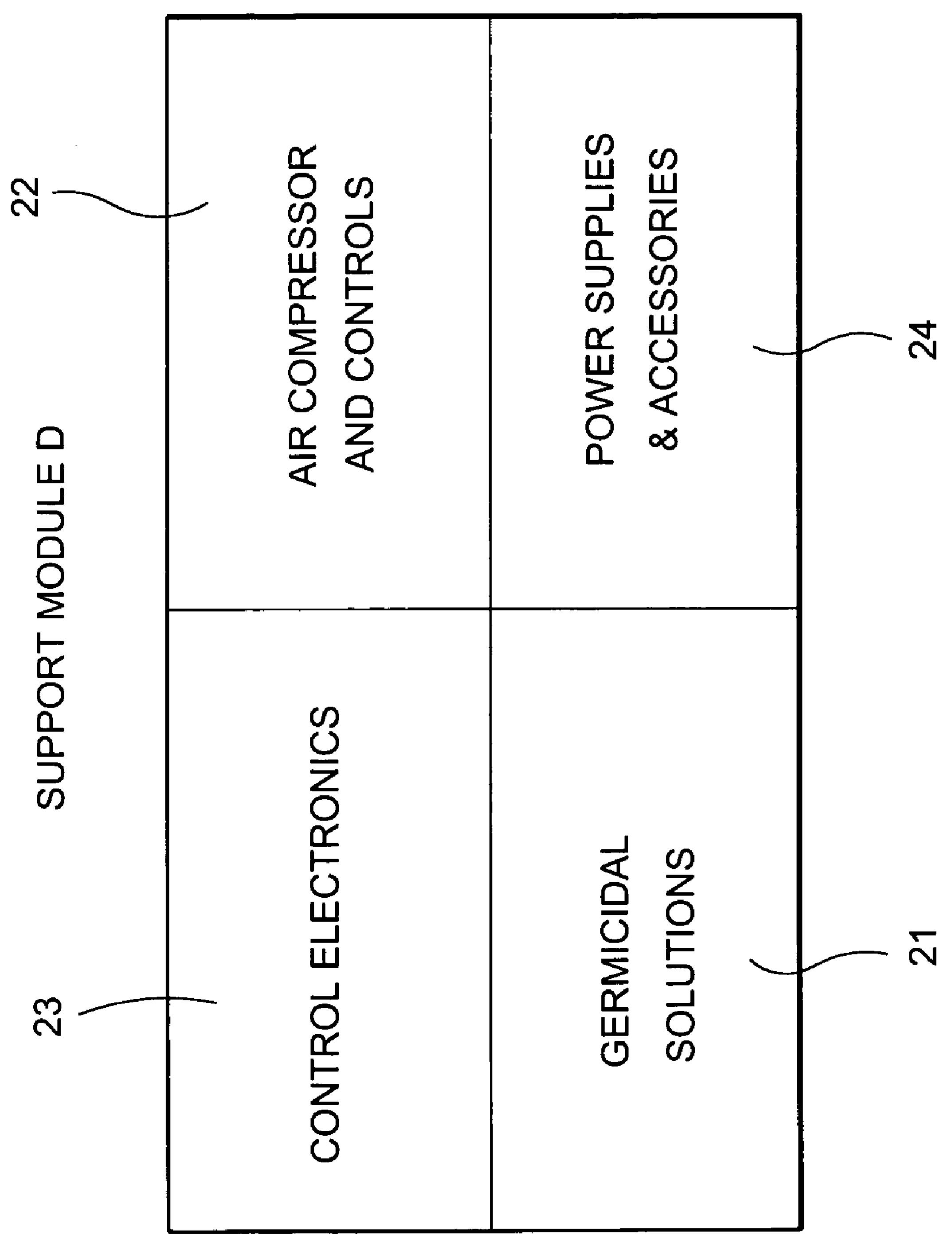
FIG. 8 is a schematic view of the support module D shown in FIG. 4.

As shown in FIG. 8, Support Module D may be mobile and may comprise a germicidal particulate supply 21, a small air compressor 22, interface cables, accessories and manuals 23, power supplies and accessories 24 and/or a vacuum (not shown). The Modules A, B and C may be removably connected to each other and to the Module D in any suitable manner.

In accordance with the method of the present invention, a final extended preventative measure may be the spraying on or application of a quick drying germicidal film on the former contaminated surfaces. This would provide a long term protection from any undesirable elements reestablishing themselves. The selection of the film would be based on effectiveness against the largest number of primary undesirable elements and the potential for their reoccurrence.

Safety is of primary importance. The present invention will incorporate appropriate audio and visual alarms, fail safe interlocks, automatic shut down, decals, operator emergency override control and any other necessary safety features. Guarding against direct viewing of the UVC radiation is of primary importance as permanent eye damage can possibly result from such viewing. For example, if a module is turned upside down and has a UVC subunit installed, then a mercury switch or the like would be installed to turn OFF the UVC immediately.

Figure 9:
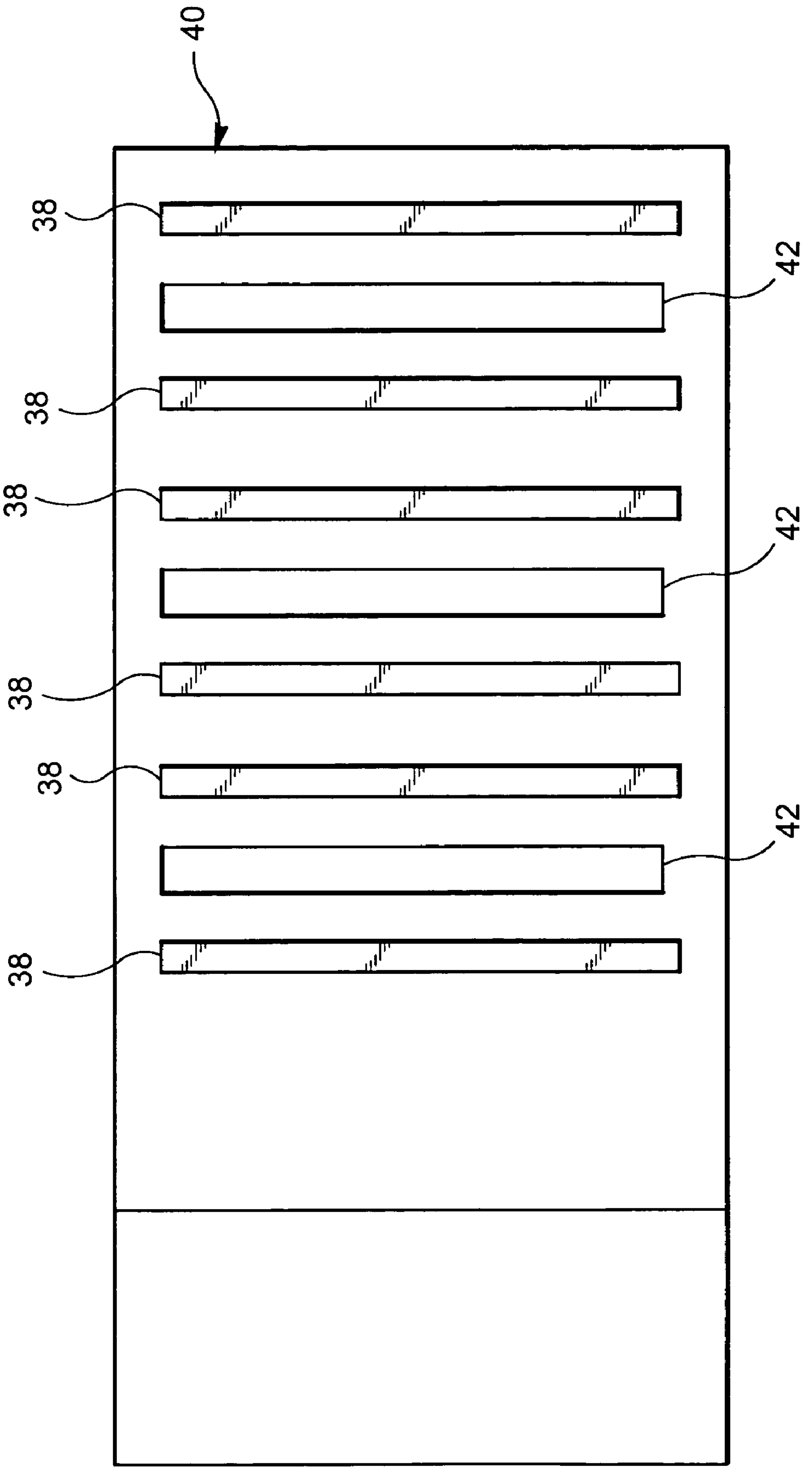
FIG. 9 is a schematic view of a third embodiment of the present invention in the form of a trailer or pod configuration.
Figure 10:
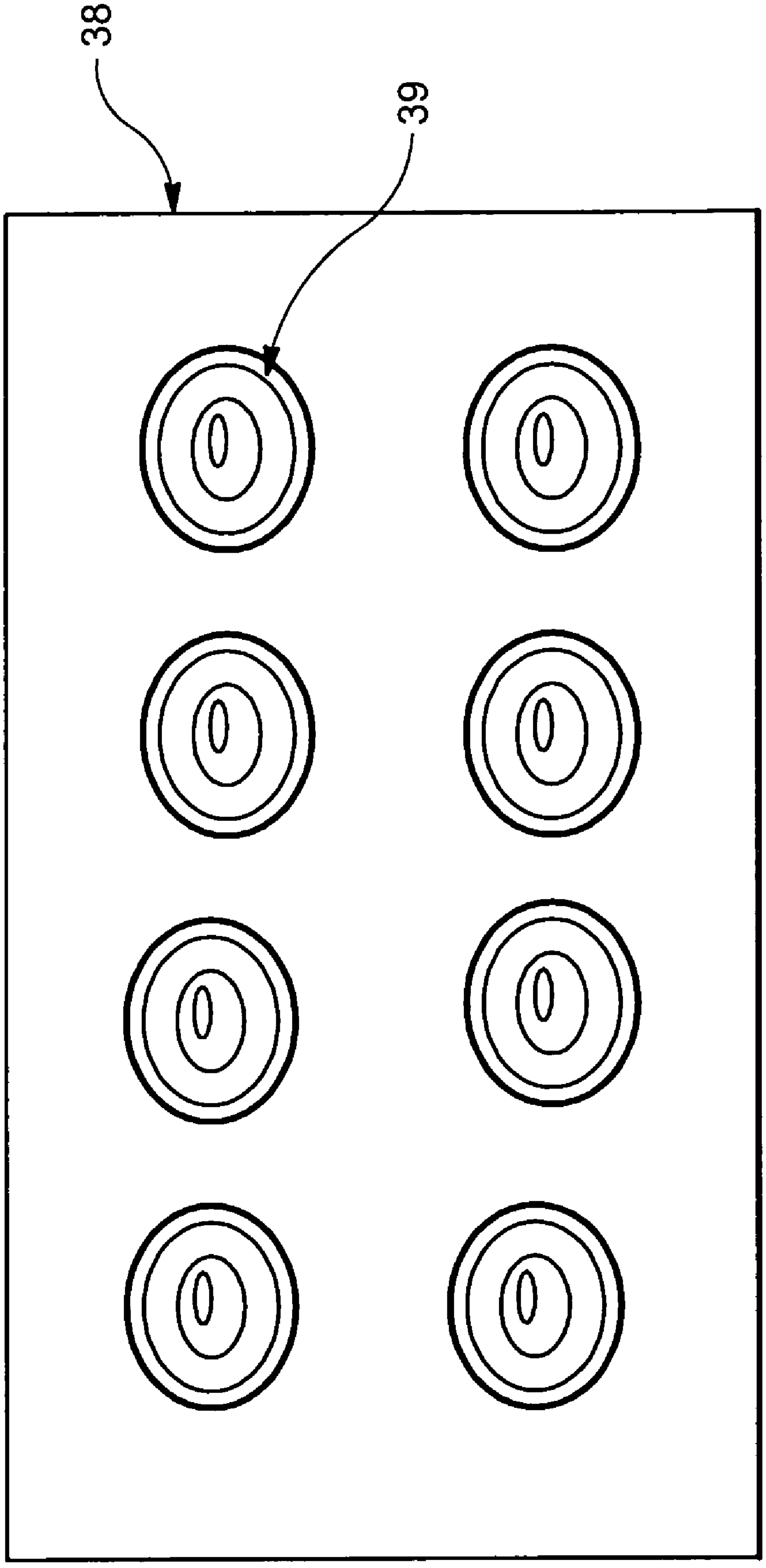
FIG. 10 is a schematic view of an eradication technology panel of the embodiment shown in FIG. 9.

FIGS. 9 and 10 illustrate a third embodiment of the present invention in the form of a trailer or fixed pod or housing 40 having one or more slots, openings or frames 42 therein for the insertion of a large object, such as a mattress or the like, to be treated. Each of the openings 42 is provided with one or more panels 38 having mounting points 39 thereon for dual or multiple technology eradication units. The large objects to be treated can be moved through the openings in the trailer or pod for the eradication of undesirable elements, such as undesirable organisms or insects. Alternatively, the article to be treated can be fixedly mounted in the trailer or pod and the eradication units can be moved along the article to be treated.

From the foregoing description, it will be apparent that the new and improved eradication system is simple in construction, effective in operation, flexible in use and possesses many advantages over the prior art such as the following:

1. Provides apparatus and methods of neutralizing and destroying (eradicating) disease elements in a manner not currently being used, such as those described herein.

2. Use of miniaturized plug-in modules to allow for quick changes of applied technology and thereby ensuring that the best technology is used for any situation.

3. Selection of different size units allows for the user to be proactive to infestations of any size.

4. Control of treatment is directed toward actual problem areas and are not splattered in the area.

5. There are no residual products e.g., film, odors, heat, cold, or the like.

6. It is easily adaptable to site conditions with minimum disruptions and no special site preparation.

7. It can readily incorporate new technology without total system replacement.

8. The simple operation requires minimum training and allows quick reaction.

9. No toxic chemicals or materials are used.

10. It can be configured to exact and desired conditions and concerns.

11. There is less lost time when it is used.

12. It does not require the area being treated to be sealed or have the temperature set at a higher or lower level.

13. The low cost allows units to be readily available to apply to specific problems. It does not require timely or costly coordination.

14. It provides for the destruction of undesirable elements in certain materials in areas, e.g., cracks and crevices, not possible or readily achieved heretofore.

15. It incorporates safety features not available in current types of extermination methods.

16. It is constructed to be adaptable and useable on any materials of different sizes, patterns and compositions.

17. It can use a wide variety of germicidal materials in solid form.

18. It comprises an adaptable technological construction which can be packaged in modular mobile form and thereby allows for processing materials in place or can be a large size system using the same technology fixed in place with the materials to be treated being brought to the system.

19. It provides for real time assessment of the effectiveness of the treatment and thereby allows for a repeated treatment if necessary with greatest efficiency.

20. It is inherently adaptable to using newer developments in germicidal products by the use of special design eradicator subunits suitable for mounting in the modules.

21. It does not require a special enclosure to conduct treatment.

22. It allows for use of a variety of eradication technologies singularly or in multi-mixes for greatest effect under different conditions and type of elements to be eradicated.

23. It allows for immediate use of the area and materials targeted or in area of the extermination treatment.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. Apparatus for eradicating or neutralizing undesirable elements such as organisms or insects in a particular article to prevent harm to humans or animals coming in contact with or exposed to the article, said apparatus comprising:

a pair of modular units removably connected to each other, and a mobile support unit constructed to removably support and be connected to said modular units, one of said modular units comprising a source of ultraviolet radiation for killing or neutralizing the undesirable elements on the surfaces of the article, and the other said modular units comprising a source of an eradication technology treatment other than ultraviolet radiation for further killing, neutralizing and/or driving out and exposing undesirable elements, wherein each of said modular units comprises a miniaturized unit constructed to be plugged into the other modular unit and the support module.

2. The apparatus of claim 1 wherein, said other eradication technology treatment of said other modular unit is selected from the group consisting of pulsed or steady state ultrasound, hypersonic waves, non-contact ultrasonic and/or direct contact ultrasonic, application of ferrous micro-particles by ultrasonic means; quantum cascade laser; infrared light, UV-C LED, laser diode and electro-magnetic field force or any combination thereof.

3. The apparatus of claim 1 further comprising a third modular unit removably connected to said pair of modular units and to said mobile support unit, said third modular unit comprising a source of ultraviolet radiation for killing or neutralizing exposed undesirable elements on the article.

4. The apparatus of claim 1 wherein said support module comprises control electronics, air compressor and controls, germicidal solutions, power supply and accessories or a vacuum source for said modular units.

5. The apparatus of claim 1 wherein each of said modular units comprises handles for facilitating the movement thereof.

6. Apparatus for eradicating or neutralizing undesirable elements such as organisms or insects in a particular article to prevent harm to humans or animals coming in contact with or exposed to the article, said apparatus comprising:

a pair of modular units removably connected to each other, and a mobile support unit constructed to removably support and be connected to said modular units, one of said modular units comprising a source of ultraviolet radiation for killing or neutralizing the undesirable elements on the surfaces of the article, and the other said modular units comprising a source of an eradication technology treatment other than ultraviolet radiation for further killing, neutralizing and/or driving out and exposing undesirable elements, wherein said one modular unit comprises an elongated housing having an open side, a source of ultraviolet radiation extending longitudinally through said housing and positioned to direct ultraviolet radiation toward said open housing side, a track extending longitudinally through said housing, and a closed circuit video camera slidably mounted on said track and facing said open housing side.

7. The apparatus of claim 6 further comprising a servo motor mounted on said housing and connected to said video camera for moving it along said track.

8. The apparatus of claim 6 wherein said housing has a viewing window in the side thereof opposite to said open side.

9. The apparatus of claim 6 wherein said other modular unit comprises an elongated housing having an open side, a first track extending longitudinally through said housing, a second track extending longitudinally through said housing and spaced from said first track, said source of an eradication technology treatment being slidably mounted on said first track and facing said open side and a closed circuit video camera slidably mounted on said second track and facing said open side.

10. The apparatus of claim 9 wherein servo motors are mounted on said housing and are connected to said source of eradication technology treatment and said video camera to move them along said first track and said second track, respectively.

11. The apparatus of claim 9 wherein said housing has a viewing window in the side thereof opposite to said open side.

* * * * *